United States Patent

Beran

[11] 4,324,235
[45] Apr. 13, 1982

[54] ENDOTRACHEAL TUBE

[76] Inventor: Anthony V. Beran, 3802 Teakwood, Santa Ana, Calif. 92707

[21] Appl. No.: 133,014

[22] Filed: Mar. 24, 1980

[51] Int. Cl.³ ............................................. A61M 25/00
[52] U.S. Cl. ............................. 128/207.15; 128/349 B
[58] Field of Search ....................... 128/207.14, 207.15, 128/348, 349 R, 349 B, 349 BV, 350 R

[56] References Cited

U.S. PATENT DOCUMENTS

| | | | |
|---|---|---|---|
| 3,707,151 | 12/1972 | Jackson | 128/349 B |
| 3,862,635 | 1/1975 | Harautuneian | 128/207.15 |
| 3,890,976 | 6/1975 | Bazell et al. | 128/207.15 |
| 4,214,593 | 7/1980 | Imbruce et al. | 128/349 B |
| 4,278,081 | 7/1981 | Jones | 128/207.15 |

Primary Examiner—Henry J. Recla
Attorney, Agent, or Firm—Grover A. Frater

[57] ABSTRACT

An endotracheal tube is fitted with a leak preventing cuff. The cuff encompasses the tube and is made self-inflating by opening a respiratory gas flow passage through the tube wall from the interior of the tube to the interior of the cuff. The function of the tube is enhanced, and safety is improved, by molding the distal end of the tube.

3 Claims, 5 Drawing Figures

U.S. Patent  Apr. 13, 1982  4,324,235
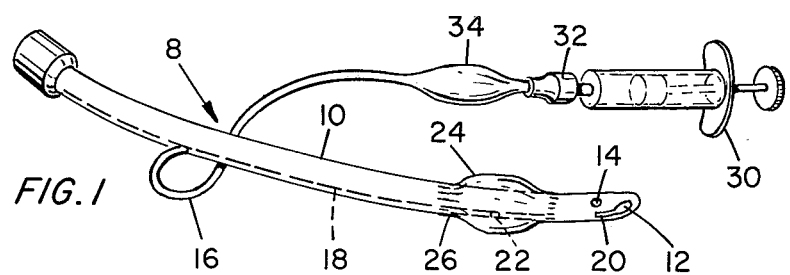
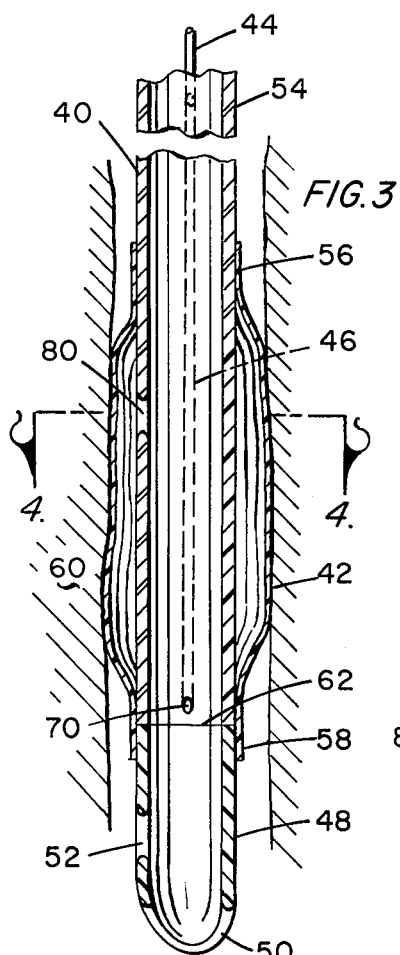
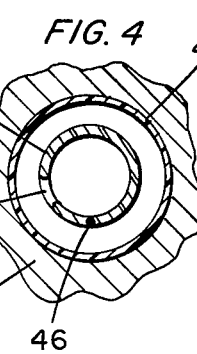
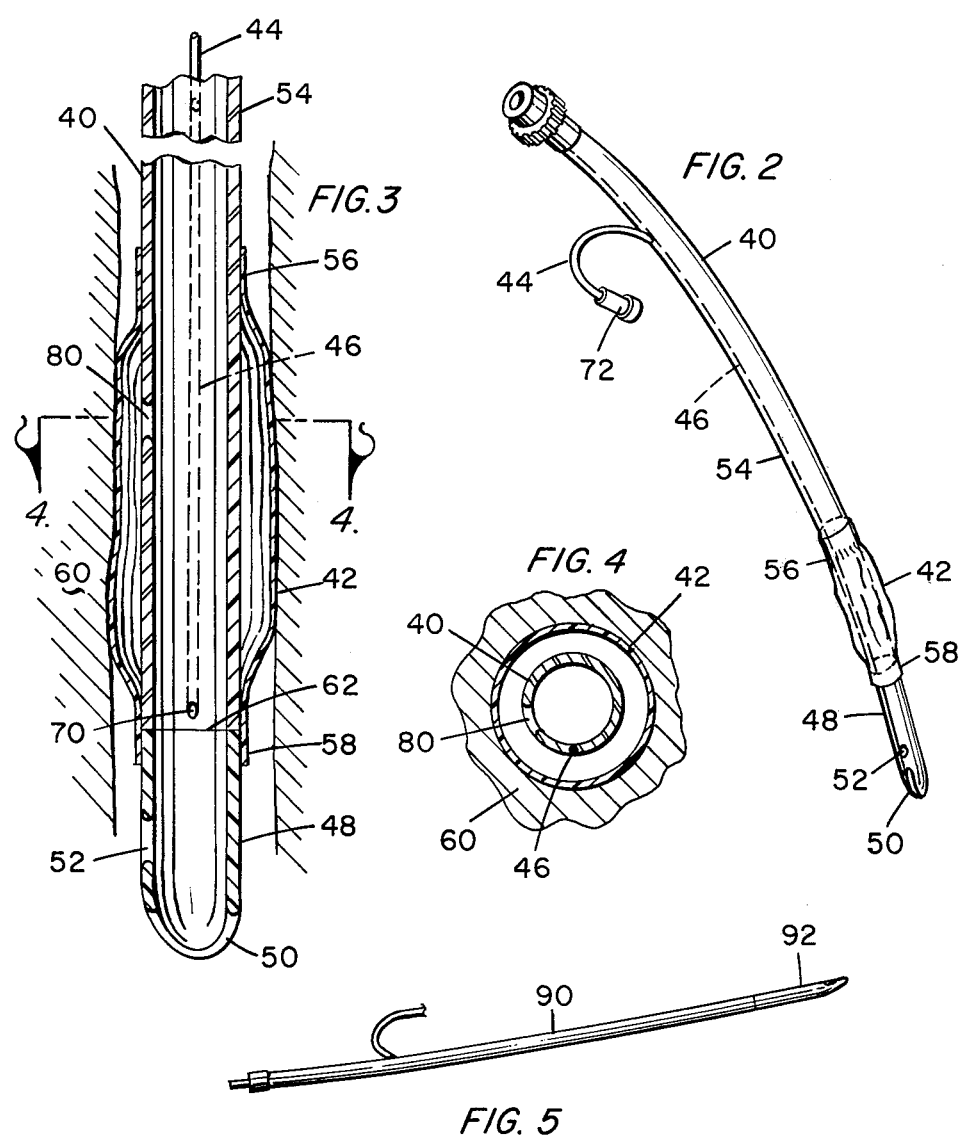
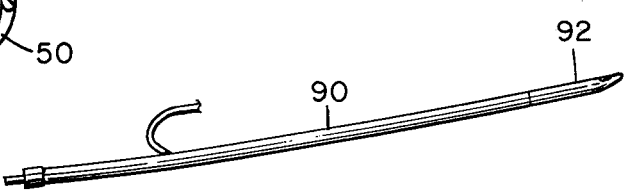

ENDOTRACHEAL TUBE

This invention relates to improvements in endotracheal respiratory tubes and to improved inflatable cuffs for such tubes.

BACKGROUND OF THE INVENTION

Endotracheal tubes are inserted in the trachea of patients and the outer end is connected to a source of respiratory gas. Such tubes are available in a number of sizes each to fit a different sized trachea. However, it is not possible to match supply tube and trachea size sufficiently, to prevent the outflow of respiratory gas around the outside of the tube. To prevent such flow, some supply tubes are fitted with an inflatable annular balloon which surrounds the respiratory gas flow tube and is commonly called a "cuff." In what has become the standard form of endotracheal tube, an auxilliary tube or passageway is included inside the respiratory gas supply tube. This auxilliary passage opens to the interior of the cuff and extends inside the respiratory gas flow tube to a point near the supply end. At that point, a separate tube is brought through the wall of the respiratory gas flow tube where it is connected to a syringe or other implement by which air may be forced into the cuff.

Such cuffs are entirely effective to prevent leakage past the end of the tracheal tube if inflated in sufficient degree. They present a problem, however, if the cuff is overinflated. The cuff will, in that case, press against the tracheal wall and damage its tissue. Often, the tube by which the cuff is inflated includes, or is connected to, an accumulator balloon. The appearance or the feel of the accumulator provides an indication of the pressure level in the cuff. Use of the accumulator is of some use in avoiding injury to the trachea but only at the expense of added complexity. A check valve is required in the filling line along with some means for violating the check valve or otherwise relieving the pressure in the cuff.

Cuffs fall into one of two classes. Some of them are made of a resilient material formed such that, in relaxed condition, the cuff remains ballooned to larger diameter than the flow tube. The other kind of cuff is formed of a substantially pliant material which exhibits little resilience, at least in the sense that it can be inflated without stretching the material from which the cuff is formed.

The fact that the inflatable cuff can cause injury has not gone unnoticed. A number of attempts have been made to find a self-inflating cuff whose inflation would be accomplished by "back pressure" exerted by respiratory gas and, therefore, would apply a pressure to the trachea that was related to supply pressure. These self-inflating cuffs operate like parachutes or, when made of resilient material that tends to balloon outwardly, with a combination of umbrella and parachute action. However, none of these self-inflating forms have found acceptance, apparently because of non-uniformity in their performance and because of failure to inflate until back pressure reaches a relatively high value.

Whether the end tracheal tube includes a cuff or not, it has been almost universal to form the respiratory gas supply tube from a length of tubing which is cut to length usually by cutting the inner distal end on the bias. Modern tubes often include a hole formed by punching through the side wall of the supply tube near the bias opening. The added opening is often called a "Murphy eye" and its purpose is to ensure that there can be a flow opening even if the bias opening becomes blocked. Any failure to eliminate sharp edges at the bias opening and Murphy eye presents a further opportunity for injury to the trachea tissue.

The invention provides an improved inner end for tracheal tubes and an improved cuff and cuff inflating arrangement.

SUMMARY OF THE INVENTION

It is an object of the invention to provide an improved endotracheal tube. It is an object to provide an endotracheal tube which has an improved, closed cuff and to provide a cuff inflating arrangement that eliminates the need for the inflation tube and the accumulator and the check valve and the air syringe that have been required in the past.

It is a further object to provide an endotracheal tube which has an inner end that is improved in that it is formed with uniformly smooth edges and surfaces, and which is made non-transparent to X-rays in a degree that is more uniform than has been possible in the past.

The improvement of the inner end of the tube is accomplished by molding at least the inner end of the tube and by including a material in the inner end which is opaque or translucent to X-rays. The molding process permits full control of the shape of the tube around the bias opening and the Kelley opening.

The cuff is improved and simplified so that damage as a consequence of overinflation is not possible. The invention recognizes that leakage past the endotracheal tube is undesirable only during that portion of the breathing cycle when gas is being supplied to the patient. It matters not that there is leakage past the endotracheal tube during expiration. That means that the cuff need be inflated only during the supply portion of the cycle.

The pressure gradient along the endotracheal tube during the supply portion of the breathing cycle is small, but there is a difference between the pressure at the inlet or supply end of the endotracheal tube and the pressure in the region near its inner end. Similarly, the dynamic pressure at the exterior of the endotracheal tube in the region surrounding the cuff will be less than the pressure within the tube in the region of the cuff, except to the extent that the pressure at the exterior of the cuff results from pressing on the cuff by the trachea. If a means is provided for permitting flow of respiratory gas from the endotracheal tube into the cuff, gas will flow from the tube into the cuff, inflating the cuff until pressure at the interior of the cuff is opposed by an equal force exerted by the tracheal tissue. The magnitude of those opposing forces will depend upon the pressure at the point along the endotracheal tube at which supply gas is taken for inflating the cuff. In the preferred form of the invention the cuff is located near the inlet end of the endotracheal tube, where it is ordinarily positioned, and communication between the interior of the cuff and the interior of the endotracheal tube is afforded by forming an opening in the supply tube wall under the cuff. In that region, the pressure within the endotracheal tube is equal to or is only slightly above pressure in the lungs so that it is only a small amount above the pressure in the trachea in the region surrounding the cuff. The result is that the cuff is inflated sufficiently so that it applies a pressure against the trachea wall but only in a degree sligthly greater than what that pressure would be if the cuff was omitted and the trachea wall was subjected only to the pressure of respiratory gas.

In the invention, the pressure that is applied to the tissue of the trachea is not some arbitrary value that depends upon the subjective estimate of an attendant who has the means at hand to apply excessive pressure to the cuff. In the invention, inflation pressure varies with the pressure of respiratory gas and never exceeds the pressure of the respiratory gas, except only slightly. Inflation and pressure are reduced at each exhalation. The result is that the tissue of the trachea is subjected to pressures which, for practical purposes, are no greater than what would be applied by the respiratory gas supply system itself. Much of the opportunity for doing harm either by underinflating or overinflating the cuff is eliminated and, of course, all of the additional inflating apparatus that is employed in the prior art is rendered unnecessary.

A further object is to provide a low pressure cuff whose operation is uniform and reliable and is generally independent of the position it occupies in the trachea or individual differences in trachea shape or size. To this end the invention provides a closed cuff which has no opening to the exterior of the endotracheal tube but communicates only with the interior of that tube.

THE DRAWINGS

In the drawings:

FIG. 1 is an isometric view of a prior art endotracheal tube with a cuff and the apparatus for inflating the cuff;

FIG. 2 is an isometric view of a preferred form of this invention;

FIG. 3 is a cross-sectional view, taken on a longitudinal center plane, of the portion of the apparatus of FIG. 2;

FIG. 4 is a cross-sectional view, taken on line 4—4 of FIG. 4; and

FIG. 5 is a view in elevation of a fragment of an alternative form of endotracheal tube according to the invention.

DESCRIPTION OF THE DRAWINGS

The prior art device selected for illustration in FIG. 1 is typical. The endotracheal tube is generally designated 8. Its primary port is a transparent respiratory gas supply tube 10 of plastic material which is flexible but sufficiently rigid so that it does not collapse and so that it is assumes the curved configuration, when in relaxed condition, as it is shown to have in FIG. 1. The upper third of the tube 10, the supply end, is not of interest and has been omitted. The inner end is open, and the opening 12 is formed by cutting the tube on the bias. Adjacent to that end opening 12 is another opening 14 in the side wall of the tube. Opening 14 is customarily provided in endotracheal tubes and it is called a "Murphy eye." Its purpose is to ensure that there is a flow path for respiratory gas, even if the end opening 12 should become blocked.

The inner wall of the tube 10 is circular in cross-section, except that at one side a second, inner tube, having much smaller diameter, is extruded with the inner wall of the larger tube over its length. At a point along its length, about one-third from the upper or supply end of the tube, an opening is made in the wall of supply tube 10 so that access is had to the interior of that small inner tube. The end of a small diameter pressurizing tube 16 is inserted into that opening and is bonded in situ so that the interior of the tubing 16 communicates with the interior of the inner tube of the supply tube 10. That inner tube is indicated in FIG. 1 by the dashed line 18. At its inner end, tube 18 is sealed closed with a body of material 20 which is opaque to X-rays. Any of a number of known materials may be used for that purpose. In this example, about one centimeter of the inner end of the inner conductor 18 is so filled.

At a point five or six centimeters away from the inner end of the supply tube 10, there is an opening in the supply tube wall which affords communication from the interior of the inner tube 18 to the exterior of the supply tube. That opening is visible in FIG. 1, where it is numbered 22, notwithstanding that the portion of the supply tube to which it opens is surrounded by a cuff 24 of transparent material.

The cuff is tubular. Its ends have reduced diameter to form sleeves which are bonded to the outer surface of the supply tube at respectively associated ends of the cuff. The outer sleeve, the one closest to the source end of the supply tube, is bonded to the tube in the region designated 26. The inner sleeve of the cuff is bonded to the exterior of the endotracheal tube in the region designated 28. Between the two regions, 26 and 28, the cuff surrounds the tube and is ordinarily spaced from it in small degree when the cuff and the tube are in relaxed condition. The opening 22 lies between regions 26 and 28 so that the cuff 24 can be inflated to larger diameter by forcing air into the cuff through the external pressurizing tube 16, the internal passageway of inner tube 18, and the flow opening 22. If the plunger of the syringe 30 is withdrawn from the connector 32, and is adjusted so that the syringe contains several cubic centimeters of air, and is then reinserted into the coupling member 32, the air from the syringe can be forced into the cuff 24 by depressing the plunger of the syringe. That air will fill the cuff and the passageway 18 and tube 16 and an accumulator 34 which is shown as an enlargement of the tube 16 at the point at which it is fastened to the coupler 32. The coupler includes a check valve which prevents air from escaping from the coupler 24 and the accumulator 34 and the remainder of the system when the syringe 30 is removed. To deflate the cuff, the syringe 30 is removed from the coupler and a probe, such, for example, as the end of the syringe, is used to open the check valve and to permit the escape of air from the cuff and the accumulator.

The patient, who may be unconscious, ordinarily can provide no indication of what force is actually being applied to the trachea. The attendant has no information except for the appearance and the feel of the accumulator 34 and a knowledge of how much air was forced into the system at the syringe. In that circumstance, it is not uncommon for the cuff to be inflated sufficiently to impede blood flow in the tissue adjacent to the cuff, and otherwise to cause injury to that tissue.

That difficulty and that danger is entirely avoided in the apparatus of FIG. 2. Despite similarities in the appearance of that unit to the one shown in FIG. 1, there are some very major differences between them. In FIG. 2, the supply tube is designated 40. It, too, has a small tube molded into the inner surface of the tube 40 along its length, but in the case of FIG. 2, that tube is not used to inflate the cuff 42. Instead, it is used only for sensing pressure at or near the inner end of the endotracheal tube. The small diameter pressure sensing line 44 has its end inserted into an opening in the wall of the tube 40.

The tube 40 is formed in two pieces in this preferred embodiment. The inner end portion 48 is shaped substantially like the prior art device in that it has the same diameter as the remainder of the tube, it terminates in an end opening 50 which is formed on the bias, and it includes a "Murphy eye" numbered 52. The outer end of that molded end 48 is abutted against the inner end of the outer section 54 of the tube and bonded in a manner described below.

The cuff 42 in FIG. 2 is formed of a transparent plastic material. When inflated it assumes tubular shape and it encompasses the supply tube. The upper end of the cuff is formed as a sleeve 56 which embraces the supply tube and is bonded to it. At the opposite end of the cuff, at the inner end, the cuff has reduced diameter to form a sleeve in the region 58 which embraces the upper portion of the molded end 48 and the inner end of the tube 54. That is, the inner end of the cuff forms a sleeve which embraces the junction between tube 54 and tube end 48 in the region 58. The cuff is made of a material which is non-resilient in the sense that it need not stretch during inflation. Instead, it is made of a pliant material which normally collapses against the outer surface of the tube 54. The sleeve unfolds and becomes distended when inflated with little or no stretching.

The cuff 42 is inflated by the flow of respiratory gas from the interior of the supply tube through an opening in the tube wall and thence into the space between the cuff 42 and the exterior of the tube 40. In the case of FIG. 1, the cuff 24 was inflated by gas flow not from the supply tube itself but from the inner passageway 18 from a source independent of the respiratory gas. In the unit of FIG. 2, the cuff 42 is inflated by gas flow not from the auxiliary passageway, and not from any external source. It is inflated by flow of respiratory gas directly from the interior of the supply tube into the cuff.

The construction of the tube and the cuff can be better understood by reference to FIGS. 3 and 4. In this figure, the endotracheal tube has been inserted into a trachea the wall of which is indentified by the numeral 60. The outer portion 54 of the endotracheal tube ends abruptly at the junction line 62 where the tube 54 abuts against and is bonded to the upper or outer rim of the molded tube end 48. The small auxiliary inner tube 46 is clearly visible in both FIGS. 3 and 4. Its wall is molded integrally with the wall of tube 54. The end of tube 46 is cut off simultaneously with the cutting off of the end of tube 54 in preparation for making the junction 62. The open end of that tube 46 senses the pressure within the endotracheal tube at a point above the junction. At the right side of FIG. 3, it is seen that the sensing tube 44 enters the wall of the tube and is inserted into the tube 46. The joint is bonded so that a leak-proof, sensing flow path is formed from the end 70 of tube 46 through the pressure sensing line 44 to the connector 72 by which the sensing tube can be connected to a pressure measuring instrument.

The cuff 42 is expanded to balloon shape in FIGS. 3 and 4. It forms a sleeve that surrounds and is substantially concentric with the inner tube 54. At its outer end, the reduced diameter sleeve portion of the cuff is bonded to the tube 54. That bond occurs in the region 56. At the other end of the cuff, where it has reduced diameter to form an inner sleeve, that sleeve embraces the junction between tube 54 and the molding 48 in the region 58, as previously described.

In FIGS. 3 and 4, the cuff is shown to have been inflated as a consequence of flow of respiratory gas from the interior of the tube 54 into the annular space under the cuff 42 surrounding the tube 54. The cuff is inflated because the pressure in the trachea space surrounding the endotracheal tube is less than the dynamic pressure of the respiratory gas inside the tube. Respiratory gas flows through the tube from a supply source into the patient's lungs because the pressure at the lungs is less than respiratory gas supply pressure. If, before the cuff is inflated, there is a leakage of respiratory gas around the endotracheal tube, it will be because there is a difference in pressure at the inner end of the endotracheal tube and the outside air. There will be a pressure gradient along that path. Since that portion of the trachea that surrounds the cuff is downstream in that flow path from the interior of tube 40 adjacent to the connecting opening 80, the pressure on the exterior of the cuff must necessarily be less than the pressure at the interior surface of the cuff. As a consequence, gas proceeds from the interior of tube 40 through the opening 80 into the annular space under the cuff. The cuff is inflated until it presses against the wall of the trachea with a pressure equal to the pressure within the tube 54. That means that the maximum pressure that the cuff can apply to the interior wall of the trachea is the pressure within the endotracheal respiratory gas supply tube at a point just above its outlet opening 50 and its "Murphy eye" 54. Thus, the maximum pressure to which the tracheal wall is subjected by action of the cuff is substantially equal to what would be experienced in the ordinary supply of respiratory gas if the endotracheal tube were removed.

The advantage of this endotracheal tube over prior art devices is obvious. Not only is it unnecessary to provide the syringe and the check valve and the accumulator bottle, and the fill line 16, but the inner, auxiliary tube can be converted to the task to sensing pressure. The opportunity for injury to the tissues of the trachea is greatly reduced.

The unit of FIGS. 2, 3 and 4 has the added advantage that the inner end portion of the endotracheal tube is made by a molding process. That permits control of the character of the margins of openings 50 and 52 in far greater degree than the cutting and punching process by which those holes have been formed in the past. Further, molding the end of the endotracheal tube permits the inclusion in all of the end pieces of a material which will be translucent, and even opaque, to X-rays. That is accomplished by inclusion of metallic powders into the substance from which the end is molded. By making the end translucent to X-rays, it is possible to determine exactly where the end of the tube and the Murphy eye are located, and to understand exactly where the endotracheal cuff is positioned.

That molded end piece has merit with or without the cuff. Ordinarily, the endotracheal tubes that are used to supply respiratory gas to infants omit the cuff. FIG. 5 shows a tube 90 suitable for use with infants and which has the special molded tube end 92 but omits the cuff.

Although I have shown and described certain specific embodiments of my invention, I am fully aware that many modifications thereof are possible. My invention, therefore, is not to be restricted except insofar as is necessitated by the prior art.

I claim:
1. An endotracheal tube comprising, in combination:
a tube having a given outside diameter;
a tube end having an outside diameter corresponding substantially to said given outside diameter bonded end-to-end to one end of said tube such that axes of the tube end and the tube are substantially coincident in the region of the bond;

said tube end having been formed by being molded of a material which is non-transparent to X-rays;

said endotracheal tube being formed with an inflatable cuff including upper and lower sleeves each bonded to said endotracheal tube at respectively associated spaced regions along the length thereof; and said lower sleeve being bonded to said endotracheal tube at the junction of said tube and said tube end such that the lower sleeve is bonded both to the tube and to the tube end.

2. An endotracheal tube comprising, in combination:

a length of respiratory tubing having an inner end arranged for insertion into a trachea and an outer end for connection to a respiratory gas supply source;

a closed, inflatable cuff bonded to and surrounding the tube, the cuff including upper and lower sleeves each bonded to said tube at respectively associated spaced regions along the length of the tube;

means for inflating the cuff with respiratory gas derived from the interior of the tube near its inner end;

said means for inflating the cuff comprising an unimpeded opening extending transversely through the wall of said respiratory tube and affording communication between the interior of the respiratory tube and the interior of the cuff;

a portion of the length of said respiratory tubing at its distal end being non-transparent to X-rays; and said portion of the length of said respiratory tubing being bonded to the remainder of said respiratory tubing at a junction which underlies one of said sleeves.

3. The invention defined in claim 2 which further comprises means in the form of a flow passage opening at the inner end of said respiratory tube for sensing pressure at said inner end of said respiratory tube.

* * * * *